United States Patent [19]

Lohn

[11] 4,120,623

[45] Oct. 17, 1978

[54] PNEUMATIC VANE-TYPE MOTOR WITH BEARING RING FOR VANE TIPS

[75] Inventor: Gerd Löhn, Biberach, Germany

[73] Assignee: Kaltenbach & Voigt GmbH & Co., Biberach an der Riss, Germany

[21] Appl. No.: 794,228

[22] Filed: May 5, 1977

[30] Foreign Application Priority Data

May 14, 1976 [DE] Fed. Rep. of Germany ....... 2621486

[51] Int. Cl.² .......... F01C 1/00; F01C 13/02; F01C 21/02; F16C 35/00
[52] U.S. Cl. .................. 418/173; 418/270; 308/9; 308/DIG. 1
[58] Field of Search .......... 418/15, 173, 270; 308/9, DIG. 1

[56] References Cited

U.S. PATENT DOCUMENTS

| | | | |
|---|---|---|---|
| 2,324,903 | 7/1943 | Beckman | 418/173 |
| 2,590,729 | 3/1952 | Scognamillo | 418/173 |
| 2,918,877 | 12/1959 | Woodcock | 418/173 |
| 2,969,743 | 1/1961 | Menon | 418/173 |
| 3,158,002 | 11/1964 | Spillmann | 308/DIG. 1 |
| 3,210,848 | 10/1965 | Bizzigotti | 308/9 |
| 3,306,375 | 2/1967 | Macks | 308/9 |
| 3,309,965 | 3/1967 | Weickgenannt | 418/270 |
| 3,437,009 | 4/1969 | Goodwyn | 418/173 |
| 3,539,281 | 11/1970 | Kramer | 418/173 |
| 3,582,243 | 6/1971 | Rhine | 418/173 |
| 4,005,951 | 2/1977 | Swinkels | 418/61 R |

FOREIGN PATENT DOCUMENTS 212,492 3/1924 United Kingdom .................. 418/173

*Primary Examiner*—John J. Vrablik
*Attorney, Agent, or Firm*—Haseltine, Lake & Waters

[57] ABSTRACT

A pneumatically operated vane-type motor for driving medical or dental handpieces. A stator housing forms a rotor chamber in which a rotor is mounted, the rotor having axial slots in which rotor vanes are radially movably mounted. The rotor rotates about an axis which is parallel to but spaced from the axis of a cylindrical inner surface of the housing which is circular in cross-section. A co-axial bearing ring is rotatably mounted in the inner surface of the housing, and the inner surface of the bearing ring is engaged by the outer ends of the vanes.

1 Claim, 6 Drawing Figures

PNEUMATIC VANE-TYPE MOTOR WITH BEARING RING FOR VANE TIPS

FIELD OF THE INVENTION

This invention relates to a pneumatically operated motor for driving medical or dental handpieces and comprising a sleeve-like housing having a cylindrical inner surface which is circular in cross-section and which forms a stator, said stator forming a rotor chamber; a rotor mounted for rotation in said chamber about an axis which is parallel to but spaced from the axis of the inner surface of the housing; axially extending slots provided in the rotor; rotor vanes radially movably mounted in the slots and extending with their outer ends towards the inner surface of the housing; and air inlet and outlet means communicating with the rotor chamber for supplying compressed air to the rotor (vanes) and for discharging the air from the chamber after driving engagement with the vanes of the rotor.

When compressed air is admitted to the motor, it, passes through the inlet means into the space between the rotor and the inner surface of the housing, and moves before it the closest vane protruding furthest from the rotor, so that the rotor begins to rotate and the next vane is acted on by the compressed air. The speed of the vane-type motor may be, for example, about 20,000 to 100,000 r.p.m.

DESCRIPTION OF THE PRIOR ART

A motor of the above type is disclosed in German Offenlegungschrifft 23 04 666. When the rotor rotates, the outer ends, in contact with the housing inner surface and sliding along it, of the vanes successively acted on by compressed air are subject to a high vibration-producing loading owing to the resultant intermittently increasing and decreasing sliding friction, leakage air passing between the outer ends of the vanes and the inner surface, so that the performance of the motor is reduced. By an appropriate choice of materials, the strength and sliding properties both of the vanes and of the inner surface can be improved. However, if indurated fabric, for example, is employed as the high-strength material for the vanes, the latter swell when they become wet, for example in the sterilisation of the motor fitted into a surgical or dental handpiece, which results in blocking of the rotor. If, for example, Teflon (PTFE) is chosen as the material having good sliding properties for the vanes, rapid wear occurs owing to the low strength of this synthetic material. If, for example, nitrided steel is used as the material having good sliding properties for the housing inner surface, rusting occurs on wetting. Also, the sliding friction between the outer of the vanes and the housing inner surface causes considerable heating and disturbing noises.

It is an object of the invention to provide a pneumatic vane-type motor in which sliding friction between the outer of ends of the rotor vanes and the housing inner surface is avoided, so that the choice of material for these parts is not critical.

SUMMARY OF THE INVENTION

According to the invention there is provided a vane-type motor operated by compressed air and comprising:
a sleeve-like housing having a cylindrical inner surface which is circular in cross-section and which forms a stator, said stator forming a rotor chamber;
a rotor mounted for rotation in said rotor chamber about an axis which extends parallel to the axis of said inner surface, said axes being spaced apart;
axially extending slots provided in said rotor;
rotor vanes radially movably mounted in said slots and extending with their outer ends towards said inner surface of the housing;
air inlet means communicating with said rotor chamber for supplying compressed air to drive the rotor;
air outlet means communicating with said rotor chamber;
and a bearing ring engaged by the outer ends of said vanes and positioned between said outer ends and said inner surface of the housing, said bearing ring being rotatably mounted within and co-axial with said inner surfaces of the housing.

The air inlet and outlet means may be arranged to open directly into the rotor chamber. However, they could also open in the region of the ring end wall at one end of the bearing ring, but the bearing ring would then have to be somewhat shorter at this end than the inner surface of the housing to ensure unhindered passage of the air.

By virtue of the fact that the outer ends of the vanes in the motor according to the invention are no longer in contact with the inner surface of the housing, but with the freely expansible bearing ring, the outer ends of the vanes do not have to undergo any slideing friction, because owing to the completely harmless static friction of the outer ends on the inside of the bearing ring, the latter is driven during the rotation of the rotor. Therefore, any suitable materials, for example plastics or metal, can be chosen both for the vanes and for the inner surface of the housing and the bearing ring without regard to detrimental effects due to wear, wetting or the like. It is therefore unnecessary to use indurated fabrics or the like as the material for the vanes, so that a swelling action or difficulty in sterilisation is avoided and the dimensional accuracy of the parts of the motor can be enhanced. Due to the harmless fixed contact of the outer ends of the vanes with the bearing ring, no leakage air is lost, and hence higher speed and higher torque and hence higher output of the motor are obtained with a long useful life. The motor is further distinguished by steady, vibration-free running owing to the elimination of the sliding friction between the outer ends of the vanes and the housing inner surface.

The vanes may be held in contact with the bearing ring in known manner, for example by centrifugal force, by springs disposed in the axial, longitudinal slots in the rotor or by compressed air introduced into the longitudinal slots.

The bearing ring may be slideably mounted in the inner surface of the housing. However, in order here again to avoid sliding friction, the bearing ring may be rotatably mounted with the aid of rolling bodies, for example balls. In order to avoid the rolling noises thus set up, alternatively there may be provided an air bearing between the bearing ring and the housing inner surface comprised by a ring-shaped gap to which compressed air can be admitted. Such an air bearing has the further advantage that a completely vibration-free running of the rotor and of the air bearing is ensured.

In the case of such an air bearing, either the bearing ring may be formed with at least one passage for the supply of the ring-shaped gap with compressed air from the space between the rotor and the bearing ring, or the housing inner surface may be formed with at least one outlet aperture for the supply of the ring-shaped gap with compressed air from outside the motor. In the latter case it is desirable for the outlet aperture(s) of the housing inner surface to be connected by way of a branch duct with a compressed-air supply duct which supplies compressed air to the air inlet means (aperture(s)) opening into the rotor chamber between the rotor and the housing inner surface.

More particularly when the vanes are held in contact with the bearing ring by centrifugal force, a good driving of the bearing ring by the vanes is obtained even in the starting condition in which the contact with the bearing ring is still relatively loose if the inner surface of the bearing ring is formed with axial grooves to receive the outer ends of the vanes.

DESCRIPTION OF THE PREFERRED EMBODIMENTS

Figure 1:
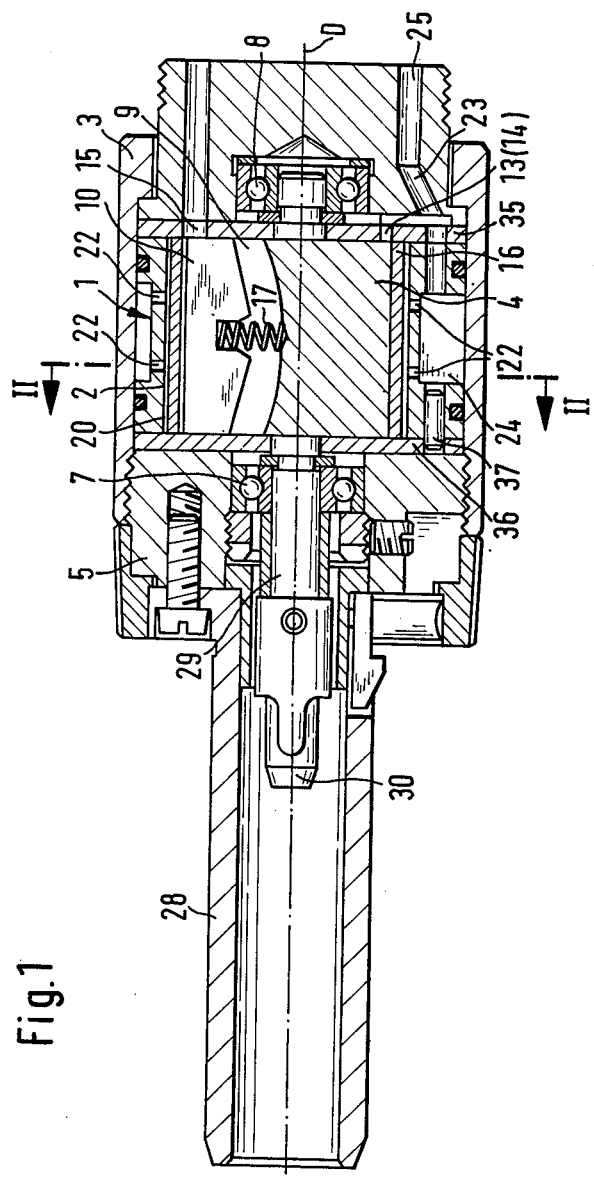
FIG. 1 is a longitudinal sectional view of a a pneumatic vane-type motor according to the invention which is suitable, for example, for a straight dental handpiece.

The illustrated pneumatic vane-type motor consists of a sleeve-form housing which has a cylindrical inner surface or wall 2 of circular cross-section and which forms the stator. The housing 1 may be surrounded by an outer casing 3, which has the form of a cylinder of circular cross-section in the case of the embodiments according to FIGS. 1, 2, 3 and 4. Disposed within a rotor chamber of the housing 1 is a rotor 4 of circular cross-section, which is mounted in end housing covers 5, 6 by means of ball bearings 7, 8. For reasons of manufacture, the axis of rotation D of the rotor 4 in the embodiments according to FIGS. 1, 2, 3 and 4 is identical with the axis of the outer casing 3. In any case, however, the axis of rotation D of the rotor 4 extends parallel with the axis A of the inner wall 2 and is offset in relation to the letter.

Mounted so as to be radially movable in longitudinal slots 9 in the rotor 4 are rotor vanes 10 whose outer ends 11 extend towards the inner wall 2.

There open into the space 12 between the rotor 4 and the circular cylindrical inner wall 2 three apertures 13, 14, 15 (FIG. 2), which are spaced apart at an angle of about 120°. When compressed air enters the aperture 13, so that the latter acts as an air inlet aperture, the apertures 14, 15 are air outlet apertures. On the other hand, when the aperture 14 receives compressed air and consequently acts as an air inlet aperture, the apertures 13, 15 are air outlet apertures. Therefore, the aperture 15 is always an air outlet aperture.

Figure 4:
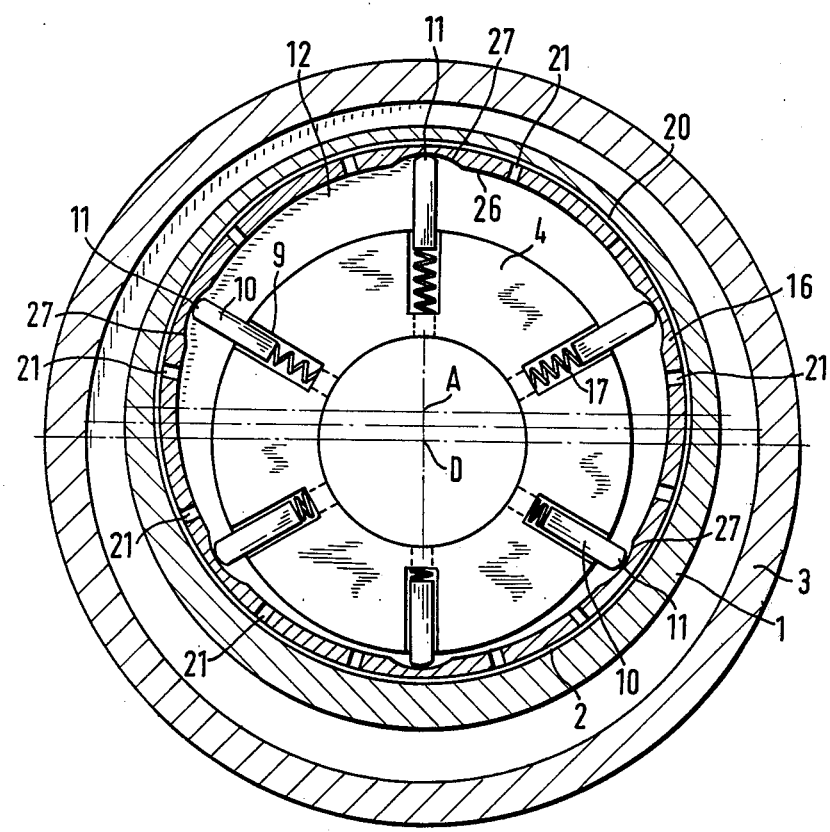
FIG. 4 is a sectional view taken along the line IV—IV in FIG. 3.

There is disposed between the inner wall 2 and the outer ends 11 of the vanes 10 a bearing ring 16 which is freely rotatable in relation to the inner wall 2 and is coaxial therewith, and against which the vanes 10 bear at their outer ends 11 under the action of compression springs 17 disposed in the longitudinal slots 9 in the rotor 4, or under the action of centrifugal force during the rotation of the rotor as shown in FIG. 4.

Figure 6:
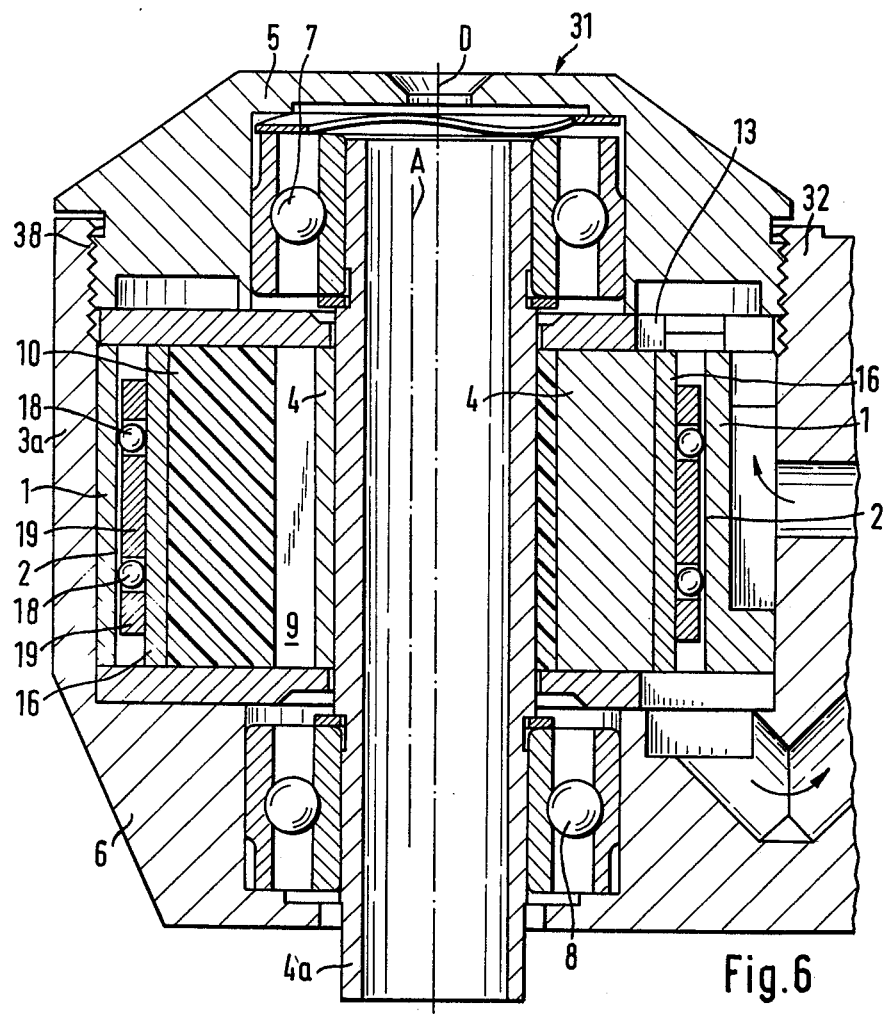
FIG. 6 is a view, similar to FIG. 5, of a further modified embodiment.

In the embodiment illustrated in FIG. 6, the bearing ring 16 is mounted on the inner wall 2 of the housing 1 by means of rolling-contact bearings 18 formed of balls, which are held in a cage 19.

In the embodiments illustrated in FIGS. 1 to 5, there is provided between the bearing ring 16 and the inner wall 2 a ring-shaped gap 20 to which compressed air can be admitted so as to form an air bearing ring 16. In the embodiments illustrated in FIGS. 3 and 4, the bearing ring 16 is formed with a number of passages 21 for supplying the ring-shaped gap 20 with compressed air from the space 12. In this way, the compressed air entering the space 12 by way of the air inlet aperture 13 (14) to act on the vanes 10 is simultaneously utilised to form an air bearing film in the ring-shaped gap 20.

Figure 2:
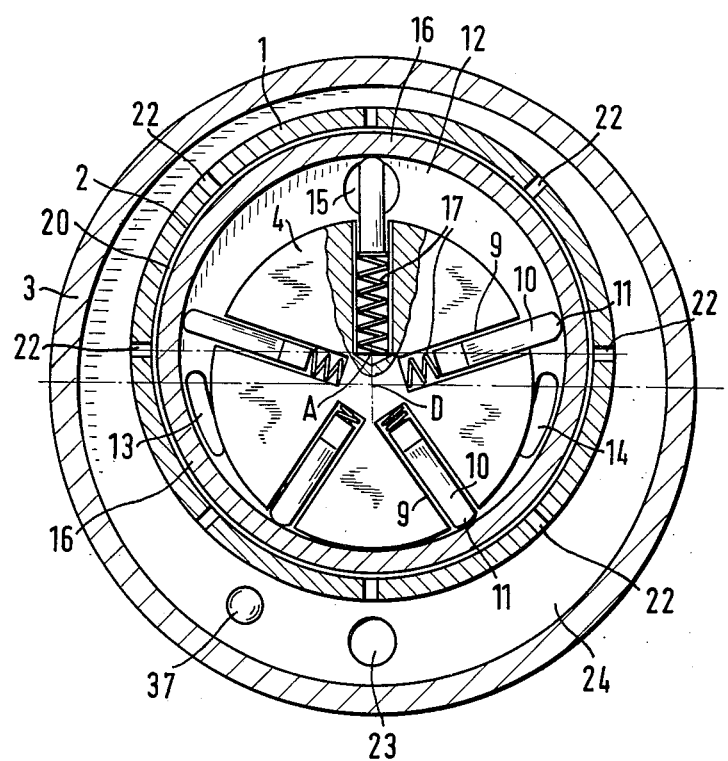
FIG. 2 is a sectional view taken along the line II—II in FIG. 1.
Figure 5:
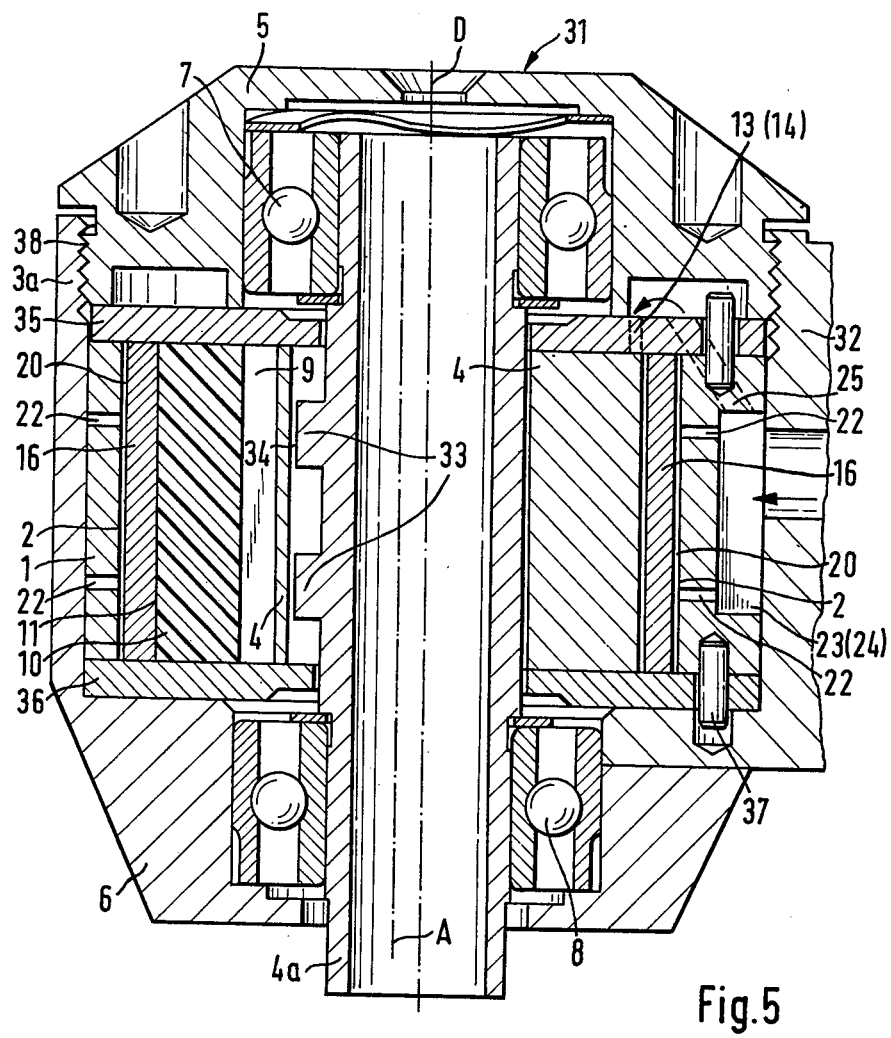
FIG. 5 is a longitudinal sectional view of a pneumatic vane-type motor which is suitable, for example, for a dental handpiece having a head extending at an angle.

Alternatively, for forming the air film for the air bearing of the bearing ring 16, the inner wall 2 may be formed with a number of outlet apertures 22 as shown in FIGS. 1, 2 and 5 to supply the ring-shaped gap 20 with compressed air from outside the motor. The outlet apertures 22 of the inner wall 2 are connected, for example in accordance with FIG. 1, by way of a branch duct 23 and a cavity 24 with a compressed-air supply duct 25 which supplies compressed air to the air inlet aperture 13 (14) opening into the space 12.

In the embodiment illustrated in FIG. 4, the inner wall 26 of the bearing ring 16 is formed with axial grooves to receive the outer ends 11 of the vanes 10.

Figure 3:
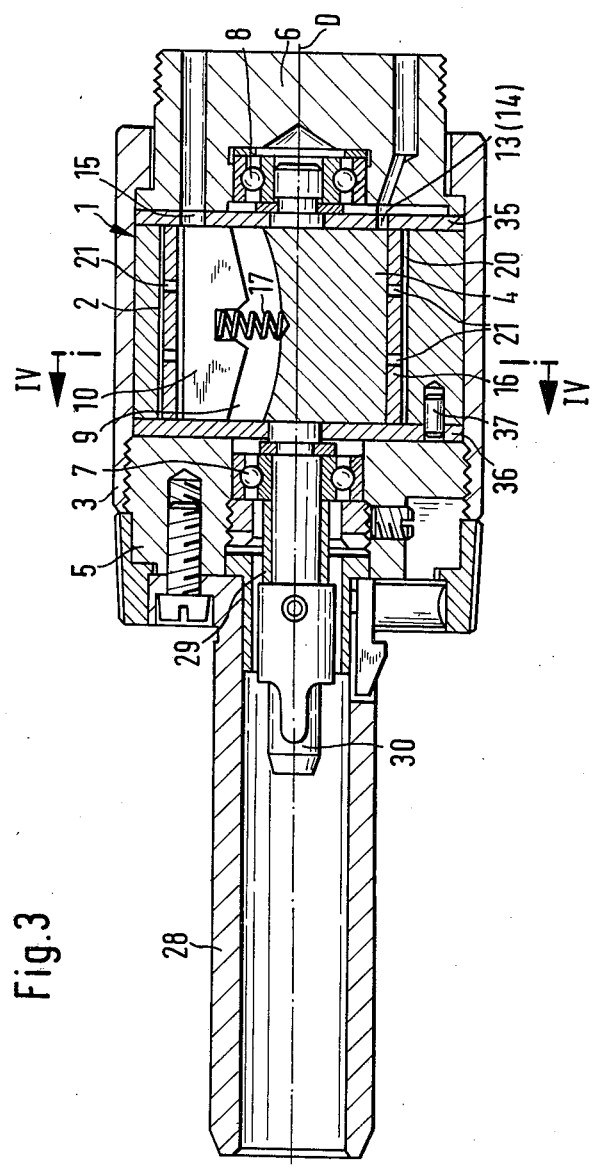
FIG. 3 is a view, similar to FIG. 1, of a modified embodiment.

The vane-type motor shown in FIGS. 1 and 3 may be used for attachment to or incorporation in a straight surgical (medical) or dental handpiece. For this purpose, there is provided a coupling sleeve 28 for connection to the handpiece (not shown). The lengthened shaft 29 of the rotor 4 is provided with a driver 30 for that end of the handpiece shaft (also not shown) which is to be coupled.

In the embodiments illustrated in FIGS. 5 and 6, the motor is incorporated in the head housing 3a of, for example, a dental angle piece having a head 31 extending at an angle. The stem of the head 31 is denoted by 32.

In the embodiments illustrated in FIGS. 5 and 6, the rotor 4 is formed in two parts. Thus, the rotor 4 also has a separate inner sleeve 4a to receive the stem of a tool (not shown), for example a drill. For a better force-transmitting connection to the actual rotor 4 and for axial securing, the inner sleeve 4a is provided with external bosses 33 which engage in corresponding recesses 34 in the inner wall of the actual rotor 4. In this way, the rotor 4 is prevented from running-on to limiting discs 35, 36 provided adjacent the housing cover 5, 6. In accordance with FIGS. 5 and 6, the housing cover 5 is screwed to the head housing 3a by means of a screwhead 38. The head housing 3a and the lower housing cover 6 form an integral component part.

As shown in FIGS. 1, 2, 3 and 5, the housing 1 having the inner wall 2 is held fast by means of a fixing pin 37 on one limiting disc 36.

I claim:

1. A pneumatic vane-type motor for a dental handpiece to drive a dental tool, comprising: a sleeve-shaped motor housing located in the outer surface of said handpiece and forming a stator; a circular-cylindrical inner surface of said housing; a rotor within said inner surface and having a rotary axis parallel to the axis of said cylindrical inner surface, said axes being spaced apart; a power take-off shaft connected to clutch means for driving said dental tool; axially extending grooves in said rotor; rotor vanes radially and movably mounted in said grooves and extending with their outer ends towards said circular cylindrical inner surface; air inlet means for compressed air and air outlet means discharging into a space between said rotor and said circular cylindrical inner surface; a bearing ring located between said circular cylindrical inner surface and said outer ends of said rotor vanes, said bearing ring being freely rotatable and coaxial with said inner surface; said bearing ring having an inner surface contacting said vanes at their outer ends in said axial grooves; annular gap means located between said bearing ring and said circular cylindrical inner surface, said annular gap means comprising an air cushion bearing for said bearing ring and receiving compressed air via a plurality of circumferentially spaced passages in said motor housing; a compressed-air supply line and a branch line; said passages being connected via said branch line to said compressed-air supply line, said air supply line supplying said air inlet means, said air inlet means discharging into said space between said rotor and said circular cylindrical inner surface.

* * * * *